United States Patent [19]

Keller et al.

[11] Patent Number: 4,543,328
[45] Date of Patent: Sep. 24, 1985

[54] PROCESS FOR DETECTING PATHOGENS

[75] Inventors: Franz Keller; Hans Hennemann, both of Würzburg, Fed. Rep. of Germany

[73] Assignee: Boehringer Mannheim GmbH, Mannheim, Fed. Rep. of Germany

[21] Appl. No.: 190,540

[22] Filed: Sep. 24, 1980

Related U.S. Application Data

[63] Continuation of Ser. No. 973,280, Dec. 26, 1978, abandoned.

[30] Foreign Application Priority Data

Jun. 16, 1978 [DE] Fed. Rep. of Germany ....... 2826416

[51] Int. Cl.$^4$ ........................ C12Q 1/24; C12Q 1/29; C12Q 1/04; C12M 1/00
[52] U.S. Cl. ........................................ 435/30; 435/29; 435/31; 435/34; 435/287; 435/800; 435/803

[58] Field of Search ....................... 435/29, 30, 31, 34, 435/287, 292, 296, 284, 800, 803; 128/214 R, 214 C, 214.2; 210/DIG. 23, 503, 504, 506, 508, 509, 510, 446, 502, 287, 289

[56] References Cited

U.S. PATENT DOCUMENTS

| | | | |
|---|---|---|---|
| 2,682,268 | 6/1954 | Ryan et al. | 128/214 R |
| 3,803,810 | 4/1974 | Rosenberg | 128/214 R X |
| 3,875,012 | 4/1975 | Dom et al. | 435/30 |
| 3,888,250 | 6/1975 | Hill | 128/214 R |
| 3,901,808 | 8/1975 | Bokros | 210/DIG. 23 |
| 3,993,560 | 11/1976 | Halpern | 128/214 R X |

Primary Examiner—Robert J. Warden
Attorney, Agent, or Firm—Sprung Horn Kramer & Woods

[57] ABSTRACT

Process and device for the detection of pathogens, such as bacteria, fungi and viruses, in blood in the presence of an anticoagulant agent. The pathogen is separated in an extracorporeal circulation of the blood with a biocompatible adsorbent which selectively binds the pathogen and thereafter detects by bacteriological, mycological, virological or electron microscopic methods.

19 Claims, 1 Drawing Figure

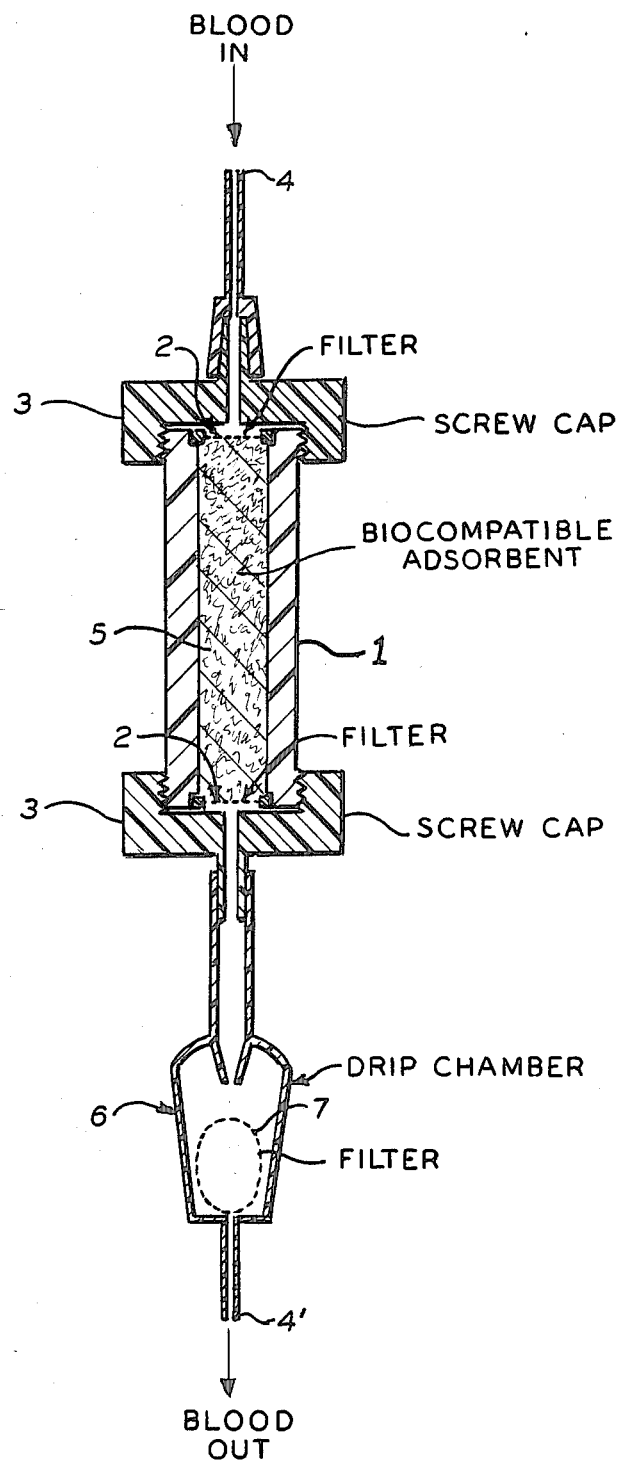

PROCESS FOR DETECTING PATHOGENS

This is a continuation of application Ser. No. 973,280, filed Dec. 26, 1978, now abandoned.

BACKGROUND

The present invention relates to a process and device for the detection of pathogens, such as bacteria, fungi and viruses, in blood.

Today, septic complications are one of the chief causes of death of patients who are in intensive care units because of an otherwise serious illness. The causes are the weakened resistance to infection due to the fundamental disease and the inability completely to prevent infection by pathogens from other patients.

Today, more than 60 antiobiotics from 13 different groups of preparations provide the possibility of taking positive action against diagnosed pathogens. An early diagnosis and thus an improved possibility of therapy can decisively improve the chances of survival of patients suffering from a bacterial or mycotic attack of the system.

Diagnosis of sepsis is provided by the clinical picture (fever, shivering, leukocytosis, leftward shift in the differential blood picture and consumption coagulopathy, as well as septic shock and other non-specific signs) and from the cultured detection of micro-organisms in the blood of the patient. In the case of a positive detection of micro-organisms, the antibiogram also gives important indications for the most effective antibiotic or antimycotic therapy. The bacteriological detection processes which are today conventional are essentially only technical variants of the blood culture techniques developed at the turn of the century. By means of the introduction of the liquoid venules and of the blood culture bottle with previously prepared nutrient substrate, a relative optimization of the well-known processes was achieved. However, for clinical purposes, the results obtained with these processes are still not satisfactory. The previous improvements of the blood culture processes were limited to the development of more sensitive bacteriological detection techniques. This applies not only to the radiometric measurement of marked carbon dioxide but also to membrane filtration methods and the further developments thereof.

The chance of being able to identify pathogens with the conventional blood sampling techniques for culture purposes is only 30% of all clinically certain cases, which is terribly low. This low quotient of success could, according to present day knowledge, have two causes:

1. The septic focus does not emit a continuous stream of pathogens but rather an intermittent one. The ideal point of time to obtain the pathogens from the blood circulation is prior to the appearance of clinical symptoms, such as fever and shivering.
2. A large number of patients is already treated with antibiotics. These antibiotics unavoidably pass with the pathogen into the culture medium and suppress the growth of the micro-organisms so that the blood culture can give a falsely negative result. This means that in 70% of all cases of clinically certain sepsis, the fight is against unknown pathogens and usually also without knowing whether it is a bacterial or a fungal sepsis. Thus, the choice of the correct anti-biotic or anti-mycotic is purely a matter of luck.

For years, attempts have been made to close this diagnostic loophole. New methods have been developed which are supposed to give a quicker and more certain detection of pathogens in the blood than the previously known processes. However, even in the case of these new processes, three decisive disadvantages still remain. The blood sample must still be collected at the precise point of time at which the pathogens pass into the circulation and thus, in the ideal case, before the patient shows an increase in temperature. Furthermore, only a small aliquot from the total amount of blood is used for the investigation. In the case of patients who have been previously treated with antibiotics, residues of antiobiotics are also introduced into the culture and there bring about an inhibition of the growth of the pathogens.

SUMMARY

The present invention provides a diagnostic process which does not suffer from the above-mentioned disadvantages and enables pathogens which get into the blood circulation of patients at an unknown point of time to be isolated for diagnostic purposes, possibly to remove traces of adhering antibiotics and to carry out the determination with the smallest possible expenditure of labor.

Thus, according to the present invention, there is provided a process for the detection of pathogens, such as bacteria, fungi and viruses, in the blood in the presence of an anticoagulation agent, wherein the pathogen is separated in an extracorporeal circulation of the blood with a biocompatible adsorbent which selectively binds the pathogen, whereafter the pathogen is detected by bacteriological, mycological, virological or electron microscopic methods.

DESCRIPTION OF THE DRAWING

The accompanying drawing is a cross-sectional view of a device of the invention for carrying out the process thereof.

DESCRIPTION

The principle of haemoperfusion, which forms the basis of the present invention, has long been employed for the treatment of severe states of intoxication, for example in cases of poisoning with sedatives. However, this known process is one of removing pharmaceuticals from the blood by adsorption on charcoal and is thus a purely therapeutic treatment.

It is surprising that a diagnostic process can now be made available which permits the detection of pathogens, i.e., micro-organisms, such as bacteria and fungi, as well as of viruses, without significantly changing the natural blood components, for example erythrocytes, leukocytes and thrombocytes.

In one embodiment the biocompatible material effective to selectively bind the pathogen is an adsorbent material. Various adsorbent materials can be employed. In this case the adsorbent may bind the pathogen by selective adsorption. On the other hand, the binding may be produced in other ways and may be physical or chemical in nature, the binding being such that the pathogen is bound or immobilized on the biocompatible material.

The adsorbents used are biocompatible polymers and especially polymers which are compatible with the blood and thus are haemocompatible and which selectively bind the pathogen, which adsorbents cannot only be used as such but also applied to a porous carrier. In other words, all polymers can be used which can serve not only as layer formers but also as bead material, insofar as they are sufficiently porous or can be made sufficiently porous. The porosity improves the adsorption of the pathogen when this is the means of binding, and also promotes uniform flow of the blood through a bed of the adsorbent. At the same time, the porosity permits a high rate of flow of blood through the bed.

As polymers, there can be used, for example, polyacrylates or polymethacrylates, for example polyhydroxyethyl methacrylate (poly HEMA-SPHERON, Koch Light Ltd. England. Examples of other polymers which can be used include adsorber resins, such as "Amberlite" XAD II which is a synthetic crosslinked polystyrene polymer, cellulose acetate, collodium and nylon. As carrier for the layer former, there can be used, for example, porous materials, such as glass, ceramic materials, such as clay, metal oxides, such as aluminum oxide, titanium dioxide, zirconium dioxide and silicon dioxide, or active charcoal.

Acrylic hydrogel-coated vegetable charcoal (Haemocole, Smith & Nephew, England) has proved to be a useful material. The proportion of coating material can be 0.5 to 10% and preferably to about 2% of the total weight of the adsorbent. The coating process is one which is well known in the art and thus need not be explained in more detail.

Furthermore, as adsorbent there can also be used a porous material, for example glass, coated with vapor deposited charcoal. There can also be used porous glass which has been rendered biocompatible by coupling with heparin and/or albumin, which acts anti-thrombogenically. In the case of heparin, binding can be achieved, for example, by means of a water-soluble carbodiimide. The glass used can be, for example, the so-called "controlled bor glass" (producted by Corning Glass Works and Electro-Nucleonics, Fairfield, Conn.).

Furthermore, the adsorbents can be in the form of fine particles or granules or, for example, also in the form of sheets or foils which are placed in the haemoperfusion chamber and can easily be removed and readily introduced into a nutrient substrate or nutrient solution.

The adsorbent when in particle form suitably has a particle size effective to permit satisfactory flow of blood through a packed bed of the particles while providing a contact time between the particles and the blood to permit an effective binding of the pathogen to the adsorbent.

Similarly when the adsorbent is in the form of sheets or foils, the dimensions of these are suitably selected so as to achieve the same criteria.

The volume of adsorbent will also affect these determinations.

In general, it is found convenient, when employing a particulate adsorbent to employ particles having a diameter of about $40\mu$ to about $3000\mu$ (3 mm) and a surface area ranging from about 0.01 to about 2000 $m^2/g$.

In the case of the preferred acrylic hydrogel-coated vegetable charcoal this conveniently has a particle size of 2–3 mm and a surface area ranging from about 1000 to about 2000 $m^2/g$, and preferably about 1250 to about 1350 $m^2/g$. In the case of the polyhydroxyethyl methacrylate this conveniently has a particle size of about $20-150\mu$ and preferably about $60-100\mu$ and a surface area ranging from 50 $m^2/g$ to about 200 $m^2/g$. In the case of the glass this conveniently has a particle size of about $20-150\mu$ and preferably about $60-100\mu$ and more preferably $80\mu$ and a surface area ranging from 0.05 $m^2/g$ to about 0.4 $m^2/g$ and preferably about 0.2 $m^2/g$. In conjunction with a blood flow of about of 20 to about 250 ml of blood per minute in a pressure positive perfusion; and preferably about 100 to 200 ml of blood per minute when a blood pump is employed; and with a volume defined by the particulate adsorbent of about 10–60, preferably about 20 to about 50 $cm^3$. The extracorporeal circulation is suitably conducted for about 30 to 180, and preferably about 60, minutes.

The pathogens are preferably identified in the adsorbed state. This is particularly advantageous because the adsorbent, with the pathogen bound thereon, can be introduced directly into a nutrient medium. The known microbiological, virological or electron microscopic methods of detection can be used.

For this purpose, in the case of bacteria and fungi, the adsorbent enriched with the pathogen is cultured in the following manner: using sterile forceps, about 20 to 30 adsorbent particles are gently pressed into the surface of a nutrient medium. At the same time, liquid nutrient media can be provided with a few particles. Subsequent incubation is carried out at 37° C. The further identification takes place with the usual routine bacteriological and mycological methods. In the case of viruses, use is made of egg cultures.

It is also possible to wash the adsorbent with a buffer, to remove water with alcohol, to treat with a buffered glutaraldehyde solution and to carry out the investigation by raster electron microscopy.

The present invention also provides a device for the detection of pathogens, such as bacteria, fungi and viruses, in blood, the pathogens being separated off on a bicompatible adsorbent, by selective adsorption, in an extracorporeal circulation and detected by microbiological, virological or microscopic methods. This device, one embodiment of which is illustrated in the accompanying drawing, comprises a column 1, both ends of which are open, which contains a biocompatible adsorbent which selectively binds pathogens. In column 1 the adsorbent 5 is held in place by filters 2 with slipped-over caps 3, the caps having openings with connections for blood inlet tube 4 and blood outlet tube 4'.

The caps 3 can, for example, be constructed in such a manner that they can be screwed on to the column. In any case, they must be easily removable, without any danger of contamination, in order to permit a rapid and easy emptying of the contents, which is very important. The blood outlet can be provided with a transfusion piece 6, such as a conventional drip chamber, containing a filter 7. Inert and easily workable synthetic resins, such as polytetrafluoroethylene, can be used for making the components of the device.

The device intended for purely diagnostic purposes advantageously has small dimensions. The column can have a diameter of about 1 to 3 cm., a height of about 2 to 10 cm. and a volume of about 5 to about 100 $cm^3$. Due to the small volume, none of the theoretically possible side effects, such as a drop of blood pressure, thrombocytopaenia, loss of immune globulins, adsorption of administered medicants and haemolysis, are initiated.

All told, the device according to the present invention is of small volume and, therefore, is clinically unobjectionable, which is a significant technical advance. The device can be used quickly and easily, it is not expensive to produce and thus it can be used as a disposable article.

In the embodiment of the capsule device according to the present invention illustrated in the accompanying drawing, all the component parts are preferably made from "Teflon" and can thus be sterilized in an autoclave at 130° C. The capsule is filled with particles of vegetable charcoal encapsulated with acrylic hydrogel and, after rinsing through with physiological silane, sterilized in an autoclave at 130° C.

Animal experiments

For a comparison of the effectiveness of a conventional blood culture with a culture from perfusion charcoal, there was first used an animal experiment, the experimental animals being Wistar rats with a body weight of 250 to 300 g. Experimental sepsis was simulated by the intraveneous injection of definite numbers of *Candida albicans* cells. The entry for the haemoperfusion was by means of polyvinyl chloride tubes into the iliac blood vessels. The animals were narcosed with diethyl ether. Further investigations were carried out on awake animals in restriction cages.

At a rate of flow of 1-2 ml./minute, rat blood was removed via a roll pump from the iliac artery, passed through the charcoal-containing capsule and returned to the iliac vein. The capsule contained 3 g. acrylic hydrogen-coated vegetable charcoal (Haemocol) and the residual blood volume of the system was 3 ml. At the commencement of the experiment, the system was filled with fresh blood from a donor animal. At the commencement of the perfusion, the animals were anticoagulated with 100 IU heparin, the subsequently necessary haparinization being based upon the Lee-White coagulation time.

Sixty minutes after the intraveneous injection of 1 ml. of the Candida supsension, an arterial blood culture was first taken, followed by perfusion for a period of one hour. After conclusion of the haemoperfusion, the active charcoal was washed under sterile conditions with Ringer's solution. One part of the charcoal particles was used for a culture experiment and the other part, after fixing with glutaraldehyde Soerensen buffer, was used for a raster electron microscopic investigation.

Cultural diagnosis

The bacteriological preparation of the perfusion charcoal from the animal experiments took place in such a manner that immediately after conclusion of the animal experiment, the perfusion charcoal was removed under sterile conditions and prepared bacteriologically.

Using sterile forceps, about 20 charcoal particles per plate were distributed on a solid nutrient medium and gently pressed into the surface thereof. Saboraud-maltose agar was employed as nutrient medium for the original culture and liquid Saboraud nutrient medium was used for the enrichments. As a control for the recognition of any possible contamintion, there were simultaneously employed blood agar plates and MacConkey nutrient media. Cast plates were prepared by pouring liquefied agar medium over about 20 charcoal particles distributed over the bottom of a Petri dish.

On the 2nd, 4th and 8th days, from the liquid enrichments (thioglycolate, glucose bouillon), material was inoculated over on to the same nutrient medium in solid form as was employed for the original cultures.

Preparative technique for the raster electron microscopic investigation

After removal from the capsule, the charcoal particles were fixed for 24 hours in a 2 to 3% glutaraldehyde solution buffered at pH 7.2.

The fixed material was subsequently washed in frequently changed buffer solution and dehydrated in an increasing series of alcohol. From the pure alcohol, the preparations were transferred in at least 4 stages into Frigen 11 (trichloromonofluoromethane) (alcohol/Frigen 11: 2/1, 1/1, 1/2 and pure Frigen 11) and preserved in a pressure vessel according to the critical point method.

After applying the charcoal particles to the sample plate of the raster electron microscope, an electrically conductive layer was applied by means of a sputter device. The investigation was carried out with a Stereoscan Mark IIA (Cambridge Instruments Ltd., England).

With the diagnostic haemoperfusion, in contradistinction to the previously discussed techniques, the attempt is made to achieve an optimization of the material under investigation. The subject being investigated hereby remains connected to the extracorporeal circulation for a comparatively long period of time so that the pathogen, after its dissemination, must be captured by the charcoal capsule "trap".

The experiments on rats carried out with the diagnostic haemoperfusion device display a greater sensitivity of the perfusion method, in comparison with the liquoid venules. Supplementary experiments with gram-positive and gram-negative micro-organisms support the view that these predictions also apply to bacteria. The superior detection sensitivity manifests itself in the case of an infective dosage of $10^5$ to $10^7$ micro-organisms per animal by positive haemoperfusion in the case of the preponderantly negative liquoid venules. In the case of the liquoid venules, in two cases growth occurred at a comparatively late point of time. In one case, the cultures of the charcoal and of the liquoid venule remained negative.

It is to be stressed that the micro-organisms, in the case of the haemoperfusion method, were cultured, as a rule, directly and not by the roundabout route via a liquid enrichment. The bacteriological preparation of the charcoal particles for culturing is simple and can well be carried out in any routine bacteriological laboratory.

The stability of the binding of the micro-organisms on to the surface of the charcoal opens up the possibility of a separation of micro-organisms and adhering residues of antibiotics by means of a simple washing step.

Carrying out the process on humans

A "Teflon" capsule is filled with active charcoal coated with 2% acrylic hydrogel (Haemocole-Smith & Nephew, England), sterilized in an autoclave and attached to the patient in an extracorporeal circulation. The attachment of the capsule to the patients usually takes place by unilateral puncture of the femoral artery and the femoral vein by the Seldinger technique. The blood flows downwardly through the capsule. It is not necessary to introduce a blood pump into the system. An additional precaution against air or particle embolism is provided for by a commercially available transfusion device in the venous return. In order to prevent a thrombosing in the extracorporeal circulation, 5000

I.U. heparin are injected intravaneously before commencement of the perfusion. If it is desired to perfuse for more than 60 minutes, then further amounts of heparin are necessary, with monitoring of the Lee-White coagulation time. After a contact of any desired length of time of the flowing blood of the patient, the extracorporeal circulation is again interrupted. The active charcoal can then be freed from adhering traces of antibiotics by washing with a sterile electrolyte solution before it, together with the also adhering pathogens, is applied to a nutrient medium. In this medium, it is then possible, as described above, to identify the pathogens and to test their sensitivity to various antiobiotics and antimycotics, this testing giving concrete data concerning which preparation can presumably maintain the life of the patient.

For technically carrying out the diagnostic haemoperfusion, there are two possibilities, depending upon the clinical condition of the patient. Patients with sepsis very frequently develop an acute renal failure as a second illness. When the patient, because of renal failure, must, in any case, be treated by haemodialysis, it is sufficient simply to insert the capsule into the arterial link of the tube system of the dialysis device after the blood pump. Depending upon the circulation, there is thus ensured a contact of the charcoal with 100 to 200 ml. of blood per minute.

In the case of patients with healthy kidneys but with sepsis, another procedure has proved to be useful. The charcoal capsule is first freed from air bubbles by perfusion with a haparin-physiological sodium chloride solution (1000 I.U. heparin per 1000 ml.). The next stage is the puncturing of an artery and of a vein of the patient with synthetic resin cannulae, the minimum lumen of which should be 1.4 mm., using the Seldinger technique. The arterial puncture cannula is then connected to the upper end of the capsule and the venous cannula via a transfusion device with the lower end. After opening the clips, a further 5000 I.U. of heparin are injected into the system in order to avoid coagulation. The perfusion of the system now takes place pressure passively, i.e. without the insertion of a pump, due to the difference between the arterial and the venous pressure. The optimum period of time of the diagnostic haemoperfusion is about 60 minutes. The average flow rate in the case of the hereindescribed pressure-passive perfusion is about 30 ml./minute.

In this manner, the following advantages of the haemoperfusion method are obtained, in comparison with the previously used processes.

In comparison with the previously used blood culture technique, the haemoperfusion method has a greater detection sensitivity. Furthermore, it offers the advantage that culture results and thus the antibiogram of the resistance testing are available sooner. By means of a rinsing step after the haemoperfusion, it is possible to prevent traces of antiobiotics getting into the culture.

However, one of the main advantages is the possibility of a longer presence of the human circulation. This increases the probability of not overlooking the point of time of a dissemination of micro-organisms in the blood circulation.

In the case of previously used blood cultures, it is a disadvantage that, as a rule, they must be frequently repeated. The blood vessel entries which are necessary for haemoperfusion are often already present due to other indications, such as dialysis, cardiac surgery, arterial pressure monitoring and the like. In these situations, it is sufficient to connect the capsule with the connections already present. The introduction of the capsule into the arterial system presents no problems, especially during the course of a dialysis treatment.

Side effects due to poisoning which have been described in the case of therapeutic haemoperfusion are, in the case of diagnostic perfusion, negligibly small due to the reduced volume of the perfusion capsule. In the case of 7 patients, monitoring of the haemoglobin, of the erythrocyte, leukocyte and thrombocyte counts, as well as of the LDH activity of the serum, before and after diagnostic perfusion, showed no significant changes.

To summarize, the new system according to the present invention provides the clinician with increased diagnostic possibilities in cases of suspected septicaemia and the patient is not endangered by the diagnosis. The chances of success of obtaining a more positive result are greater than in the case of the previously known processes. Furthermore, in the case of a positive culture finding, not only the identification of the micro-organisms but also the antibiogram, are obtained earlier than hitherto.

What is claimed is:

1. Process for the detection of pathogens, such as bacteria, fungi and viruses, in blood in the presence of an anticoagulant agent which comprises: separating a pathogen in an extracorporeal circulation of the blood, by passing the blood through a sterile adsorbent which is nontoxic and inert to blood and which selectively binds the pathogen while the blood passes the adsorbent; and thereafter detecting the adsorbed pathogen while still culturable.

2. Process of claim 1 wherein the adsorbent is a polymer which selectively binds the pathogen, the polymer optionally being applied to a porous carrier.

3. Process of claim 2 wherein the polymer is selected from the group of polyacrylate, polymethacrylate, polyhydroxyethyl methacrylate, an adsorber resin, synthetic crosslinked polystyrene, cellulose acetate, collodion and nylon.

4. Process of claim 2 wherein the porous carrier in glass, a ceramic material, a metal oxide, silicon dioxide or active charcoal.

5. Process of claim 1 wherein the adsorbent is active charcoal coated wholly or partly with a polymer selected from the group of polyacrylate, polymethacrylate, polyhydroxyethyl methacrylate, an adsorber resin, synthetic crosslinked polystyrene, cellulose acetate, collodion and nylon.

6. Process of claim 5 wherein the coating amounts to 0.5 to 10% of the total weight of the adsorbent.

7. Process of claim 6 wherein the coating amounts to about 2% of the total weight of the adsorbent.

8. Process of claim 1 wherein the adsorbent is a porous material coated with vapor deposited charcoal.

9. Process of claim 8 wherein the adsorbent is glass coated with vapor deposited charcoal.

10. Process of claim 1 wherein the adsorbent is glass coupled with heparin and/or albumin.

11. Process of claim 1 wherein the pathogen is detected by bacteriological, mycological, virological or electron microscopic methods.

12. Process of claim 1 wherein the pathogen is detected in the adsorbed state by microbiological, virological or electron microscopic investigation.

13. Process of claim 12 wherein the detection of the pathogen takes place by introducing the adsorbent enriched with the pathogen into an appropriate nutrient medium and, after incubation, identification takes place by known bacteriological, mycological or electron microscopic techniques.

14. Process of claim 12 wherein the detection of the pathogen is carried out by culturing the adsorbent enriched with the pathogen in egg cultures, and thereafter identification is carried out by means of known virological techniques.

15. Process of claim 12 wherein, for the detection of the pathogen, the adsorbent enriched with the pathogen is washed with a buffer, dehydrated with alcohol, treated with a buffered solution of glutaraldehyde and investigated by raster electron microscopy.

16. Process for detecting the presence of a pathogen selected from the group consisting of bacteria, fungi and viruses, in blood, as a means of early medical diagnosis of sepsis which comprises, extracorporeally circulating blood under investigation in the presence of an anticoagulant through a bed of a sterile particulate material which is non-toxic and inert to blood and effective to selectively bind a pathogen in the blood while the blood passes the adsorbent, permitting said material to bind any pathogen in the blood, recovering the material with any pathogen found or immobilized thereon while the pathogen is still culturable, and analyzing the material to detect any bound or immobilized pathogen.

17. Process of claim 16 wherein said bed has a volume of 5 to 100 cm$^3$.

18. Process of claim 16 wherein said material comprises a vegetable charcoal coated with acrylic hydrogel.

19. Process of claim 16 wherein said analyzing is carried out bacteriologically, mycologically, virologically or by electron microscope.

* * * * *